United States Patent [19]

Arko

[11] Patent Number: 4,687,001
[45] Date of Patent: Aug. 18, 1987

[54] SUBCUTANEOUS FLUID AND CULTURE CHAMBER AND IMPLANT TECHNIQUE

[75] Inventor: Robert J. Arko, Atlanta, Ga.

[73] Assignee: The United States of America as represented by the Department of Health and Human Services, Washington, D.C.

[21] Appl. No.: 768,397

[22] Filed: Feb. 14, 1977

[51] Int. Cl.[4] .............................................. A61B 10/00
[52] U.S. Cl. .................................... 128/767; 128/769
[58] Field of Search ................ 128/2 R, 2 F, 2 W, 1.2, 128/260, 261, 217, 264, 348, 216, 263, 270, 285, 767, 768, 769; 435/292, 296

[56] References Cited

U.S. PATENT DOCUMENTS

| | | | |
|---|---|---|---|
| 2,509,241 | 5/1950 | Mende | 128/263 |
| 3,295,527 | 1/1967 | Alley et al. | 128/348 |
| 3,310,051 | 3/1967 | Schulte | 128/216 |
| 3,640,269 | 2/1972 | Delgado | 128/2 R |
| 3,791,385 | 2/1974 | Davis et al. | 128/263 |
| 3,915,171 | 10/1975 | Shermeta | 128/348 |
| 3,924,607 | 12/1975 | Bucalo | 128/2 W |
| 3,998,211 | 12/1976 | Bucalo | 128/2 W |

OTHER PUBLICATIONS

Veale, D. R. et al., *Journ. Med. Microbiol.*, vol. 8, (1975), pp. 325-335.
Turner, W. H. et al., *Journ. of General Microbiology*, (1976) 92, pp. 224-228.
*Science*, vol. 177, (1972), pp. 1200-1201.
Novotny, P. et al. (no publication data–submitted by Applicant).

*Primary Examiner*—Henry J. Recla
*Attorney, Agent, or Firm*—Browdy and Neimark

[57] ABSTRACT

A subcutaneous culture chamber for providing a priviledged site for studying infectious disease processes of microorganisms in laboratory animals consists of a pliable polyethylene cylinder with holes at each end. The cylinder can be collapsed and inserted in a flat injector of the plunger type which is employed to force the flattened cylinder through an incision in the skin of an animal into a subcutaneous site. After insertion, the chamber soon expands to operational size and the incision is closed. Thereafter the chamber is suitable for use as an infection site to study the pathogenesis and immunology of microorganisms or for obtaining, with a syringe and needle, tissue fluid usable in a serum bacteriological assay or other study.

4 Claims, 5 Drawing Figures

SUBCUTANEOUS FLUID AND CULTURE CHAMBER AND IMPLANT TECHNIQUE

FIELD OF THE INVENTION

This invention relates to apparatus and techniques for studying infectious diseases, and more particularly to subcutaneous culture chamber apparatus and techniques for in vivo testing of antigens and infectious disease agents or immunization mechanisms in laboratory animals.

BACKGROUND OF THE INVENTION

The subcutaneous implant procedure provides a priviledged site for studying the infectious disease process of microorganisms in laboratory animals. Prior to this technique there was no practical immunological model in laboratory animals for studying such diseases as *Neisseria gonorrhoeae*. By employing the subcutaneous implant procedure, animal models have been developed for *N. gonorrhoeae*, and in addition the procedure has provided the basic techniques required for studying the immunology of other microorganisms. The increased use of this procedure in microbiology has however resulted in the implantation in animals of chambers of unacceptable design, for example, glass rods, plastic test tubes, dropper bottles, polyethylene practice golf balls, and the like. These implants have produced inhumane suffering in laboratory animals and have not always given satisfactory results.

Further background will be given by examining the following U.S. prior patents and publications, which appear to represent the closest prior art relating to the present invention, found in the course of a preliminary search:

Delgado, U.S. Pat. No. 3,640,269;
Arlen, U.S. Pat. No. 3,765,414;
Schulte, U.S. Pat. No. 3,310,051;
Bardani, U.S. Pat. No. 3,921,632;
Wichterle, U.S. Pat. No. 3,971,376.

Arko, "Implantation and Use of a Subcutaneous Culture Chamber in Laboratory Animals", Laboratory Animal Science, Vol. 23, No. 1, 105-106, 1973.

Arko, "*Neisseria Gonorrhoeae*: Experimental Infection of Laboratory Animals", Science, Vol. 177, 1200-1201, 1972.

Arko, "An Immunologic Model in Laboratory Animals for the Study of *Neisseria Gonorrhoeae*", Journal of Infectious Diseases, Vol. 129, No. 4, 451-455, 1974.

SUMMARY OF THE INVENTION

Subcutaneous chambers can provide researchers with an easily accessible means of studying host-parasite relationships heretofore observed with great difficulty or only by in vitro techniques. For example, large polyethylene chambers (practice golf balls) have been implanted in rabbits to produce fluids containing antibody to viral antigens. Similar chambers have been used to study the pathogenesis and immunology of *Neisseria gonorrhoeae* infection is small laboratory animals.

In general, the technique consists of implanting a chamber subcutaneously and allowing the chamber to fill with fluid, such as a serous transudate containing white and red blood cells. The chamber becomes suitable for use as an infection site to study the pathogenesis and immunology of microorganisms, or for obtaining, with a syringe and needle, tissue fluid for use as a component in a serum bactericidal antibody assay for *N. gonorrhoeae*, for example.

Accordingly, a main object of the invention is to provide a novel and improved subcutaneous implant apparatus and technique which produces minimum discomfort to the animal host and which provides a conveniently accessible site for studying the infectious disease process of microorganisms in the animal.

A further object of the invention is to provide an improved subcutaneous culture chamber which can be easily inserted, which can expand or collapse as fluids are injected into or removed therefrom, and which makes possible the sterile collection of tissue fluid by the use of a needle and syringe.

A still further object of the invention is to provide an improved subcutaneous implant chamber which is commercially practical, which is designed to prevent the development of pressure necrosis in the host animal, and which may be installed by means of a relatively simple and safe implantation procedure.

A still further object of the invention is to provide an improved subcutaneous culture chamber which is designed to incorporate living host tissue into the wall of the chamber, thereby providing intimate contact between the chamber fluid and surrounding tissues, which is pliable and of inert material, which is designed to readily expand or collapse as fluids are injected into or removed from the implanted chamber, and which has a configuration providing for improved host animal comfort and safety by preventing the development of subcutaneous pressure necrosis resulting in subsequent expulsion of the implant.

A still further object of the invention is to provide an improved subcutaneous culture chamber substantially in the form of a flexible cylinder adapted to be inserted subcutaneously in a relatively flattened condition and to expand to its normal cylindrical shape after insertion, so as to define a culture chamber, said chamber being formed to be relatively yieldable at its end portions so as to facilitate insertion by allowing the chamber to become more flattened at its forward end portion and to become somewhat tapered and thereby facilitate inward subcutaneous travel of the flattened chamber, and also to provide greater comfort to the host animal by allowing a large degree of wall flexure at the end portions of the chamber as compared with that allowed at the intermediate portion thereof.

BRIEF DESCRIPTION OF THE DRAWINGS

Further objects and advantages of the invention will become apparent from the following description and claims, and from the accompanying drawings, wherein:

DESCRIPTION OF A PREFERRED EMBODIMENT

Figure 1:
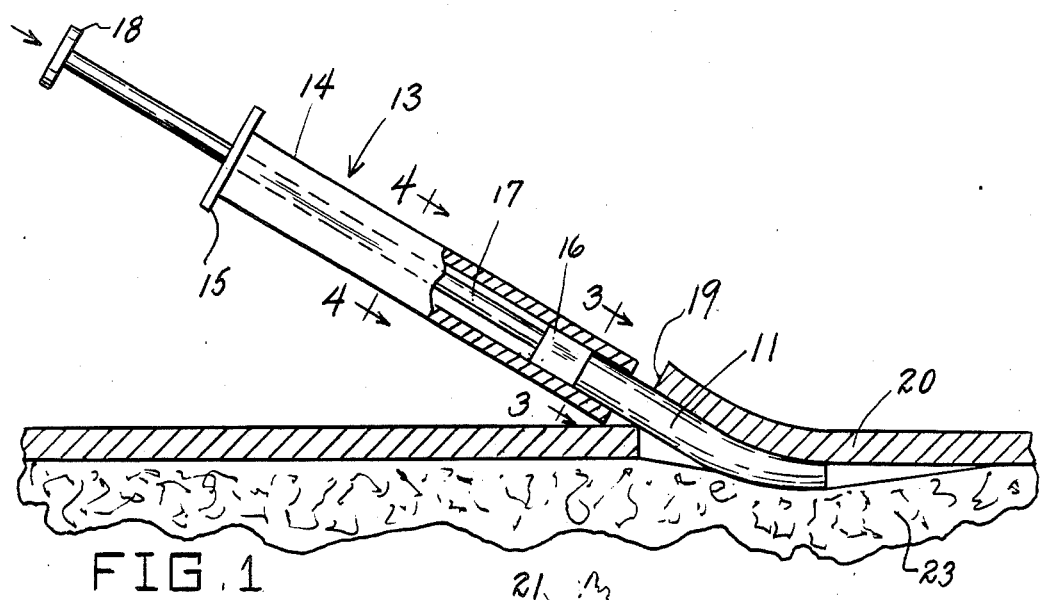
FIG. 1 is a vertical cross-sectional view, partly in elevation, showing a culture chamber according to the present invention in the process of being inserted subcutaneously in a host animal.

Referring to the drawings, 11 designates a typical subcutaneous implant culture chamber according to the present invention. Said typical chamber may comprise a polyethylene cylindrical tube of sufficiently small wall thickness to be easily flexed and soft enough to be readily penetrable by the needle of a hypodermic syringe, for example, of the order of 1 mm., but being resilient enough to tend to return to its cylindrical shape after being flattened or distorted. In a typical example, the chamber 11 is 3 cm. in length and 1 cm. in diameter. The tubular chamber 11 is formed at its opposite end portions with a plurality of evenly spaced circular apertures 12, of the order of 5 mm. in diameter. In said typical example, four evenly spaced circular apertures 12 are provided adjacent each end. The apertures 12 are employed to increase pliability and to improve animal comfort, as well as to increase the area of direct exposure of the implanted culture chamber to the surrounding tissue, to aid in incorporating living tissue into the wall of the chamber and therefore provide intimate contact between the chamber fluid and the surrounding tissue.

Figure 3:
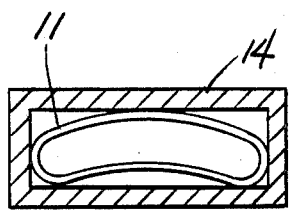
FIG. 3 is an enlarged transverse cross-ectional view taken substantially on the line 3—3 of FIG. 1.
Figure 4:
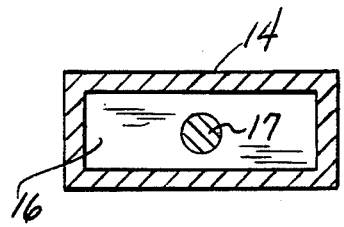
FIG. 4 is an enlarged transverse cross-sectional view taken substantially on the line 4—4 of FIG. 1.

The chamber 11 is inserted by means of a relatively flat syringe-type injector 13 comprising an elongated flat rectangular tubular main body 14 provided with an extended end wall 15 defining a peripheral gripping flange and with a rectangular plunger block 16 slidably disposed in said main body, the plunger block being rigidly connected to a plunger rod 17 which extends slidably through a central aperture in end wall 15 and which is provided at its outer end with a finger-engaging head 18. The flat tubular body 14 is shaped to receive the flattened tubular chamber 11 in the manner shown in FIG. 3 and to allow the plunger block 16 to push the flattened tubular chamber subcutaneously into the host animal, as will be presently described.

To insert the chamber 11, it is collapsed to a flattened shape and placed in the flat tubular syringe body 14. This assembly is then sterilized. An approximately 2.0 cm. skin incision is then made at the selected site of the host animal, one lip of the skin layer 20 is elevated at the incision, and the flattened chamber 11 is then forced beneath the elevated skin portion by means of the plunger block 16, namely, by forcing the plunger rod 17 downwardly relative to body 14, using gripping force between head 18 and flange element 15.

Due to the increased yieldability at the forward end of the flattened chamber 11 afforded by the holes 12, said forward end becomes somewhat tapered in profile as it is forced between the skin layer 20 and the subjacent tissue 23, as shown in FIG. 1, which facilitates its forward progress beneath the skin layer. After the flattened chamber 11 has been completely ejected from the syringe body 14 and forced beneath the elevated skin lip at the incision 19 by the plunger block 16, the elevated lip of the incision is returned to a flush closed position relative to the opposite and may be suitably held to allow the incision to heal.

Figure 2:
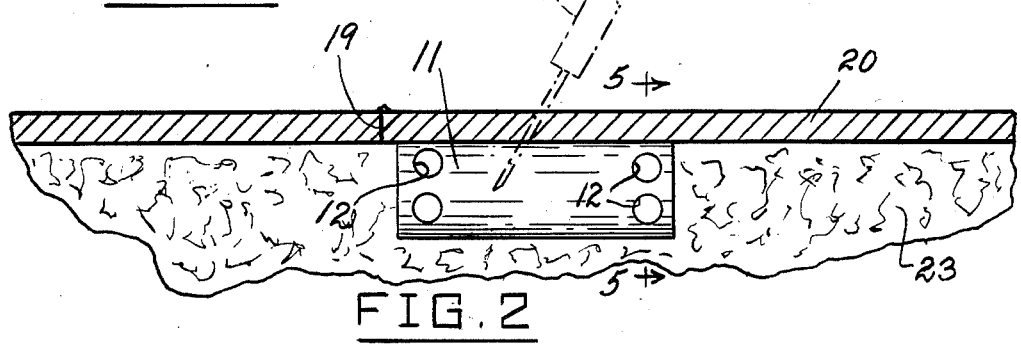
FIG. 2 is a vertical cross-sectional view showing the culture chamber of FIG. 1 in inserted position and expanded substsntially to its normal cylindrical shape.
Figure 5:
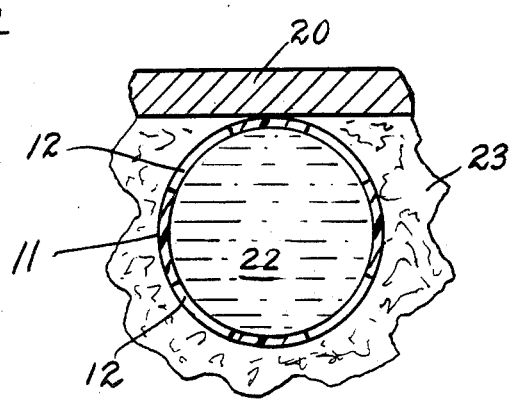
FIG. 5 is an enlarged transverse vertical cross-sectional view taken substantially on the line 5—5 of FIG. 2.

The chamber is thus allowed to expand to operational size and may eventually reach a shape close to its original cylindrical shape. In a typical embodiment, such as is shown in FIGS. 2 and 5, approximately one week after implantation the chamber 11 is suitable for use as an infection site to study the pathogenesis and immunology of microorganisms, or for obtaining, such as by a hypodermic syringe 21 with a sterile needle, biofiltered tissue fluid 22, for example, tissue fluid which may be used as a fresh complement component in a serum bactericidal antibody assay for *N. gonorrhoeae*.

The chamber 11, being of pliable material, is adapted to expand or collapse as fluids are injected into or removed from the implanted chamber. This makes possible the sterile collection of moderate amounts of tissue fluid by using a conventional hypodermic syringe 21.

As above mentioned, the subcutaneous culture chamber 11 is provided with multiple openings 12 which, together with the open ends of the chamber, allow the incorporation of host tissue into the wall of the chamber, therefore providing intimate contact between the chamber fluid 22 and surrounding tissues. In addition, the subcutaneous culture implant chamber 11 consists of pliable inert material and is designed to expand or collapse as fluids are injected into or removed from the implanted chamber. The yieldable-end configuration of the implant provides for greater host animal comfort and safety by preventing the developement of subcutaneous pressure necrosis resulting in subsequent expulsion of the implant.

The purpose of the subcutaneous culture chamber implant is to provide an immunologically priviledged site in laboratory animals for studying the host-parasite interaction in the infectious disease process of pathogenic microorganisms for which other research models are either not practical or unobtainable. By using the described chamber implant in which the host animal's subcutaneous and connective tissues form a living part of the implant wall, the natural resistance of the host to the infectious agent is temporarily reduced. This probably occurs through the selective retention from the chamber fluid of certain serum components which do not normally penetrate the wall of capillary blood vessels in the surrounding tissue. This permits the experimental disease agent to become established in an in vivo site which is accessible for repetitive sampling by needle and syringe of tissue fluid, antibodies, and cells involved in the disease process being studied. As the disease process continues, pathogenic lesions as well as humoral and cellular resistance to the disease agent develops in the fluid and wall tissue surrounding the implant, simulating the conditions that occur in some natural infectious diseases. By using the subcutaneous culture chamber implant herein described, these pathological and immunological factors can be studied in a research animal such as the guinea pig, therefor avoiding many of the medical/legal problems surrounding similar research in human subjects.

While a specific embodiment of an improved subcutaneous fluid and culture chamber and a related implant technique has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. Apparatus for establishing a subcutaneous culture chamber in a living body comprising a rigid elongated tubular sleeve member of flattened rectangular cross-section provided internally with slidable ejection plunger means fitted therein, and an elongated flexible flattened tubular member of inert resilient material of substantially uniform wall thickness normally of substantially hollow cylindrical shape and having two opposite open end portions and a plurality of relatively closely spaced apertures around its circumference at one of said end portions thereof comprising means to permit tissue encapsulation and to render said end portion substantially more yieldable than the intermediate portion of the flexible tubular member to facilitate subcutaneous insertion of the chamber and subsequent establishment of a fluid space in the adjacent body tissue, said inert resilient material being puncturable with a needle, said tubular member being held confined in said sleeve member in a substantially flattened condition so as to be engageable through an incision in the skin layer of the living body when forced out of the sleeve member by said ejection plunger means.

2. The apparatus of claim 1, and wherein said resilient tubular member is formed with a plurality of said apertures around the circumference of both of its opposite end portions.

3. An expandable and collapsible subcutaneous culture chamber for allowing the accumulation and removal of tissue fluid, and implantable in a living body beneath a skin layer through an opening cut through the skin, comprising an elongated flexible hollow tubular cylindrical member of inert resilient material, said tubular member having two opposite open end portions and a plurality of relatively closely spaced apertures around its circumference at both of said opposite end portions comprising means to permit tissue encapsulation and to render said end portions substantially more yieldable than the intermediate portion of the flexible tubular member to facilitate subcutaneous insertion of the chamber and subsequent establishment of a fluid space in the adjacent body tissue, said inert resilient material being of substantially uniform wall thickness and being puncturable with a needle, and said tubular member being sufficiently flexible and yieldable to permit its insertion beneath the skin layer in a substantially flattened condition.

4. An expandable and collapsible subcutaneous culture chamber for allowing the accumulation and removal of tissue fluid, and implantable in a living body beneath a skin layer through an opening cut through the skin, comprising an elongated flexible hollow tubular cylindrical member of inert resilient material and having a length to diameter ratio of about 3:1, said tubular member having two opposite open end portions and a plurality of relatively closely spaced apertures around its circumference at least at one end portion thereof comprising means to permit tissue encapsulation and render said end portion substantially more yieldable than the intermediate portion of the flexible tubular member to facilitate subcutaneous insertion of the chamber and subsequent establishment of a fluid space in the adjacent body tissue, said inert resilient material being of substantially uniform wall thickness and being puncturable with a needle, and said tubular member being sufficiently flexible and yieldable to permit its insertion beneath the skin layer in a substantially flattened condition.

* * * * *